(12) United States Patent
Dong et al.

(10) Patent No.: US 11,715,001 B2
(45) Date of Patent: Aug. 1, 2023

(54) WATER QUALITY PREDICTION

(71) Applicant: INTERNATIONAL BUSINESS MACHINES CORPORATION, Armonk, NY (US)

(72) Inventors: Jin Dong, Beijing (CN); Liang Liu, Beijing (CN); Zhuo Liu, Beijing (CN); Junmei Qu, Beijing (CN); Hong Zhou Sha, Beijing (CN); Wei Zhuang, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1166 days.

(21) Appl. No.: 15/942,900

(22) Filed: Apr. 2, 2018

(65) Prior Publication Data

US 2019/0303755 A1 Oct. 3, 2019

(51) Int. Cl.
*G06N 3/08* (2006.01)

(52) U.S. Cl.
CPC .................................. *G06N 3/08* (2013.01)

(58) Field of Classification Search
CPC ........ G06N 3/08; G06N 3/0445; G06N 3/084; G06N 3/0454; G01N 33/18
See application file for complete search history.

(56) References Cited

U.S. PATENT DOCUMENTS

| 2004/0256152 A1* | 12/2004 | Dashevskiy | ............ E21B 44/00 175/25 |
| 2009/0138415 A1* | 5/2009 | Lancaster | ................ G06N 5/04 706/11 |
| 2009/0294122 A1* | 12/2009 | Hansen | ................... E21B 43/25 166/250.01 |

(Continued)

FOREIGN PATENT DOCUMENTS

| CN | 100561509 C | 11/2009 |
| CN | 104318325 A | 1/2015 |

OTHER PUBLICATIONS

"Decision tree approach to build a model for water quality", Jaloree et al., Binary Journal of Data Mining & Networking 4 (2014) 25-28 (Year: 2014).*

(Continued)

*Primary Examiner* — Oluwatosin O Alabi
(74) *Attorney, Agent, or Firm* — Alexis N. Hatzis (57) ABSTRACT

This disclosure provides a computer-implemented method. The method may comprise estimating a value range of a water body parameter based on measured data for a water quality indicator of a first set of time-spatial points and measured data for the water quality indicator of a second set of time-spatial points; and determining an optimal value of the water body parameter from the estimated value range by comparing the measured data for the water quality indicator of the second set and simulated data for the water quality indicator of the second set, wherein the simulated data for (Continued)

the water quality indicator of the second set is obtained based on a fluid dynamic model using the measured data for the water quality indicator of the first set as an input of the fluid dynamic model and using a value in the estimated value range as a parameter of the fluid dynamic model.

19 Claims, 7 Drawing Sheets

(56) References Cited

U.S. PATENT DOCUMENTS

| | | | |
|---|---|---|---|
| 2010/0250216 A1* | 9/2010 | Narr | E21B 49/00 703/10 |
| 2012/0013483 A1* | 1/2012 | Jung | H04Q 9/00 340/870.16 |
| 2013/0006130 A1* | 1/2013 | Olde | A61M 1/3661 600/504 |
| 2013/0175030 A1* | 7/2013 | Ige | G05D 7/0676 700/282 |
| 2016/0018347 A1* | 1/2016 | Drbal | A61M 1/34 210/647 |
| 2016/0161310 A1* | 6/2016 | Leaders | G01F 1/663 702/48 |
| 2016/0299516 A1* | 10/2016 | Holub | G05B 15/02 |
| 2016/0364522 A1* | 12/2016 | Frey | G16B 40/00 |
| 2019/0120049 A1* | 4/2019 | Chen | G01N 33/2823 |

OTHER PUBLICATIONS

"Low-altitude remote sensing platform for estimating suspended sediment concentration in tropical cloudy environment", Fangli Zhang; Qiming Zhou, 2015 IEEE International Geoscience and Remote Sensing Symposium (IGARSS) (Year: 2015).*

"Design of a self-tuning controller for local water quality adjustment", Teng Li; Clarence W. de Silva; Sushanta Mitra, 2014 9th International Conference (Year: 2014).*

Dutta S, Jha S, Sanakaranarayanan S, Tiwari A. Output range analysis for deep neural networks. arXiv preprint arXiv:1709.09130. Sep. 26, 2017. (Year: 2017).*

Ratle F, Camps-Valls G, Weston J. Semisupervised neural networks for efficient hyperspectral image classification. IEEE Transactions on Geoscience and Remote Sensing. Feb. 17, 2010;48(5):2271-82. (Year: 2010).*

Liao H, Sun W. Forecasting and evaluating water quality of Chao Lake based on an improved decision tree method. Procedia Environmental Sciences. Jan. 1, 2010;2:970-9. (Year: 2010).*

Roehrdanz PR, Feraud M, Lee DG, Means JC, Snyder SA, Holden PA. Spatial models of sewer pipe leakage predict the occurrence of wastewater indicators in shallow urban groundwater. Environmental Science & Technology. Feb. 7, 2017;51(3):1213-23. (Year: 2017).*

Millie DF, Weckman GR, Paerl HW, Pinckney JL, Bendis BJ, Pigg RJ, Fahnenstiel GL. Neural net modeling of estuarine indicators: Hindcasting phytoplankton biomass and net ecosystem production in the Neuse (North Carolina) and Trout (Florida) Rivers, USA. Ecological Indicators. Aug. 1, 2006;6(3):589-608. (Year: 2006).*

Ding et al., "The Use of Combined Neural Networks and Genetic Algorithms for Prediction of River Water Quality," Journal of Applied Research and Technology, Jun. 2014, p. 493-499, vol. 12.

Gao et al., "A Review of Hydrological/Water-Quality Models," Frontiers of Agricultural Science and Engineering, 2014, p. 267-276, vol. 1, Issue 4.

* cited by examiner

WATER QUALITY PREDICTION

BACKGROUND

The present disclosure relates to water quality prediction, and more specifically, to water quality prediction based on fluid dynamic models.

Fluid dynamic models are developed to predict water qualities of water bodies such as rivers, reservoirs, lakes and estuaries. A fluid dynamic model may determine simulated data for one or more water quality indicators such as a water-flow velocity, water temperature and water level, which are related to the water quality of the water body. According to a method for water quality prediction, measured data for one water quality indicator at a certain time or position may be input to the fluid dynamic model, and the fluid dynamic model may determine simulated data for the water quality indicator at another time or position based on the measured data being input thereto. One or more parameters of the fluid dynamic model may correspond to the water quality indicator.

SUMMARY

According to one embodiment of the present disclosure, there is provided a computer-implemented method. The method may comprise estimating a value range of a water body parameter based on measured data for a water quality indicator of a first set of time-spatial points and measured data for the water quality indicator of a second set of time-spatial points; and determining an optimal value of the water body parameter from the estimated value range by comparing the measured data for the water quality indicator of the second set and simulated data for the water quality indicator of the second set, wherein the simulated data for the water quality indicator of the second set is obtained based on a fluid dynamic model using the measured data for the water quality indicator of the first set as an input of the fluid dynamic model and using a value in the estimated value range as a parameter of the fluid dynamic model.

According to another embodiment of the present disclosure, there is provided a system, which may comprise one or more processors and a memory coupled to at least one of the one or more processors. The system may further comprise a set of computer program instructions stored in the memory and executed by at least one of the one or more processors in order to perform actions of estimating a value range of a water body parameter based on measured data for a water quality indicator of a first set of time-spatial points and measured data for the water quality indicator of a second set of time-spatial points; and determining an optimal value of the water body parameter from the estimated value range by comparing the measured data for the water quality indicator of the second set and simulated data for the water quality indicator of the second set, wherein the simulated data for the water quality indicator of the second set is obtained based on a fluid dynamic model using the measured data for the water quality indicator of the first set as an input of the fluid dynamic model and using a value in the estimated value range as a parameter of the fluid dynamic model.

According to a further embodiment of the present disclosure, there is provided a computer program product. The computer program product may comprise a computer readable storage medium having program instructions embodied therewith. The program instructions may be executable by a device to perform a method. The method may comprise estimating a value range of a water body parameter based on measured data for a water quality indicator of a first set of time-spatial points and measured data for the water quality indicator of a second set of time-spatial points; and determining an optimal value of the water body parameter from the estimated value range by comparing the measured data for the water quality indicator of the second set and simulated data for the water quality indicator of the second set, wherein the simulated data for the water quality indicator of the second set is obtained based on a fluid dynamic model using the measured data for the water quality indicator of the first set as an input of the fluid dynamic model and using a value in the estimated value range as a parameter of the fluid dynamic model.

BRIEF DESCRIPTION OF THE SEVERAL VIEWS OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

DETAILED DESCRIPTION

Some preferable embodiments will be described in more detail with reference to the accompanying drawings, in which the preferable embodiments of the present disclosure have been illustrated. However, the present disclosure can be implemented in various manners, and thus should not be construed to be limited to the embodiments disclosed herein.

Figure 1:
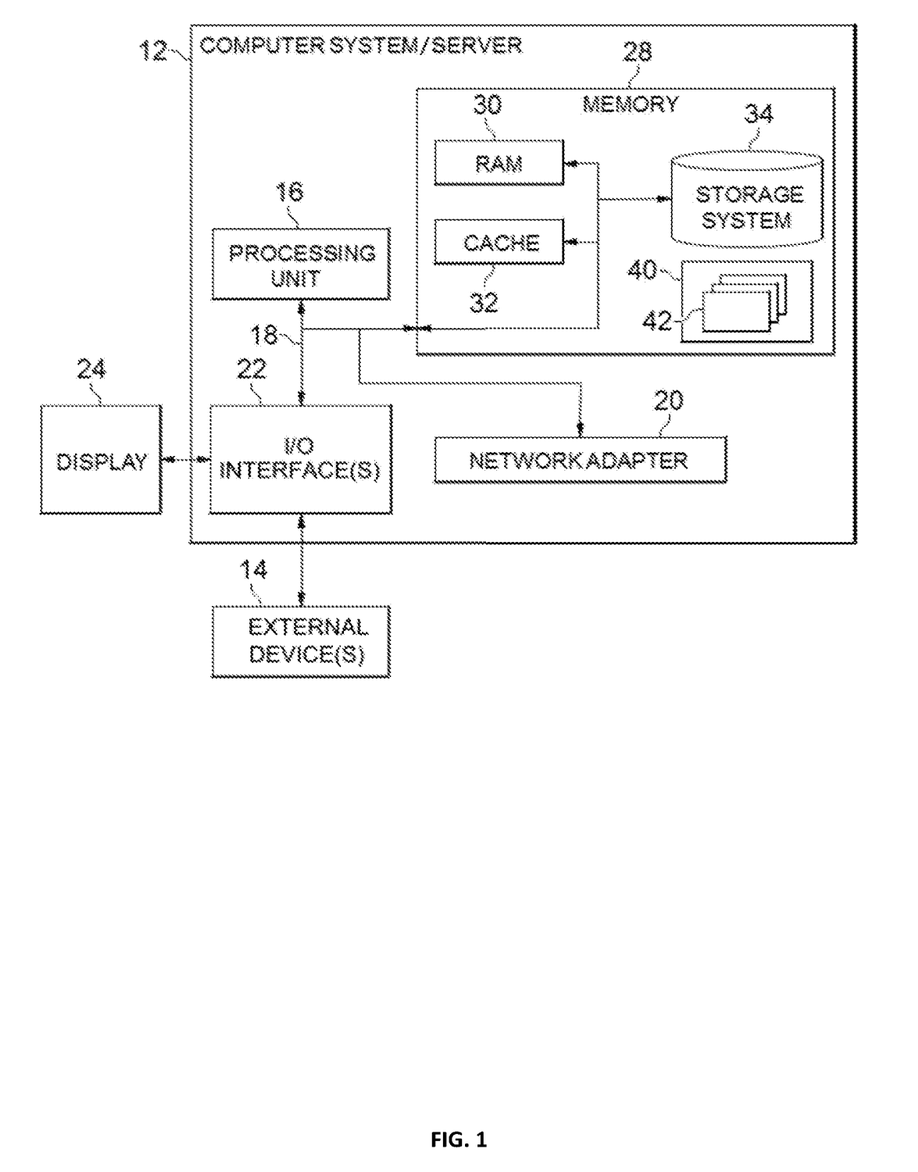
FIG. 1 shows an exemplary computer system which is applicable to implement the embodiments of the present disclosure.

Referring now to FIG. 1, in which an exemplary computer system/server 12 which is applicable to implement the embodiments of the present disclosure is shown. FIG. 1 is also adapted to depict an illustrative example of a portable electronic device such as a communication device which is applicable to implement the embodiments of the present disclosure. Computer system/server 12 is only illustrative and is not intended to suggest any limitation as to the scope of use or functionality of embodiments of the disclosure described herein.

As shown in FIG. 1, computer system/server 12 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the disclosure as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Some embodiments of the present disclosure may be implemented as the program/utility 40 or the program modules 42 of FIG. 1.

Figure 2:
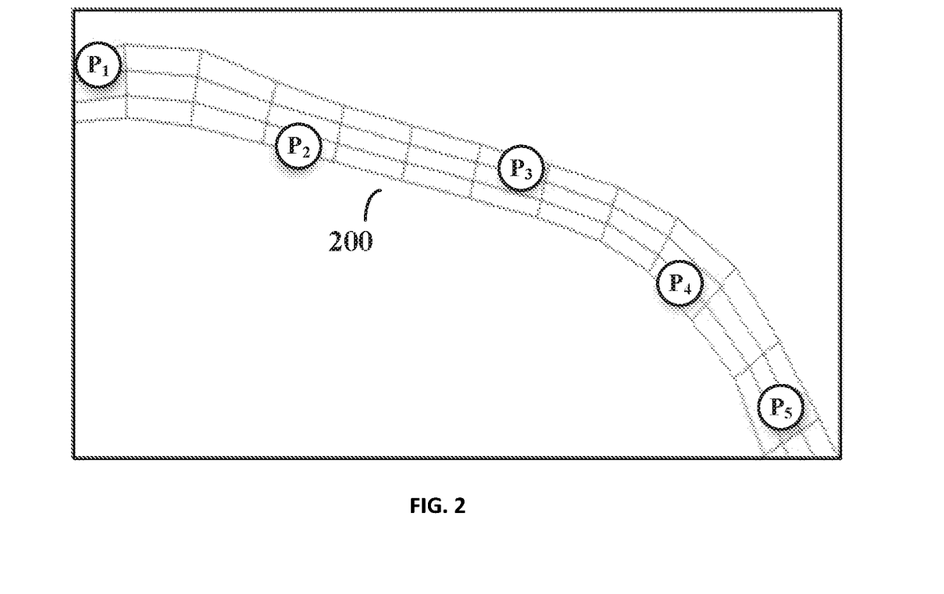
FIG. 2 is shows an exemplary water body and a plurality of positions therein.
Figure 3:
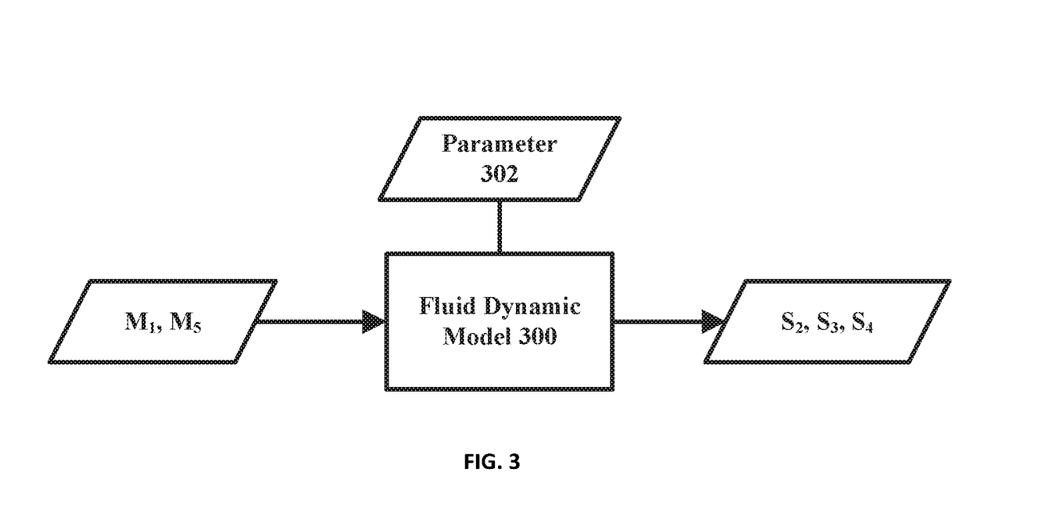
FIG. 3 is a schematic diagram showing an exemplary fluid dynamic model according to an embodiment of the present disclosure.

An example of water quality prediction will first be introduced with reference to FIGS. 2 and 3, wherein FIG. 2 shows a water body 200 with different positions $P_1$~$P_5$ therein, and FIG. 3 shows a fluid dynamic model 300 used to determine simulated data for a water quality indicator related to the water quality of the water body 200.

As shown in FIG. 2, in the water body 200, $P_1$ and $P_5$ are the starting position and the ending position respectively, and $P_2$, $P_3$, $P_4$ are positions between $P_1$ and $P_5$. Values of water quality indicators at these positions may be measured by monitoring sites located near these positions (not shown) or may be simulated using the fluid dynamic model 300 as shown in FIG. 3.

For example, in FIG. 3, measured data $\{M_1, M_5\}$ for one water quality indicator "water-flow velocity" at $P_1$ and $P_5$ is input to the fluid dynamic model 300. The following Table 1 shows $M_1=9.0$ m$^3$/s as the measured water-flow velocity at $P_1$, and $M_5=10.0$ m$^3$/s as the measured water-flow velocity at $P_5$.

The parameter 302 of the fluid dynamic model 300 is a water body parameter affecting the water quality indicator, such as a hydrology parameter or a water quality parameter, which may be recorded in the fluid dynamic model 300 in advance, and may be determined from site measurement, according to experience, or based on a large amount of statistic data from the water body 200. For example, in the case that the water quality indicator is "water-flow velocity", the parameter 302 may be a "slope", which denotes a ratio of an elevation difference and a horizontal distance from $P_1$ to $P_5$.

It should be appreciated that the parameter described herein may be one parameter or a parameter set including multiple parameters affecting the water quality indicator. The number of parameters in the parameter set may depend on which water quality indicator is to be simulated. Hereafter, one parameter may be taken as an example for simplicity, however, the parameter described herein may also indicate a parameter set.

The fluid dynamic model 300 may determine the simulated data $\{S_2, S_3, S_4\}$ for the water-flow velocity at $P_2$, $P_3$ and $P_4$ respectively based on the measured data $\{M_1, M_5\}$ and the parameter "slope". Table 1 shows the simulated data $S_2=9.3$ m$^3$/s, $S_3=9.5$ m$^3$/s and $S_4=9.8$ m$^3$/s.

TABLE 1

| | | | Simulated Data | | |
|---|---|---|---|---|---|
| $M_1$ (m$^3$/s) | $M_5$ (m$^3$/s) | Slope | $S_2$ (m$^3$/s) | $S_3$ (m$^3$/s) | $S_4$ (m$^3$/s) |
| 9.0 | 10.0 | 0.3 | 9.3 | 9.5 | 9.8 |

Further, the fluid dynamic model 300 may not only determine simulated data at different positions, but also simulated data at different times. For example, simulated data for the water-flow velocity at 3 pm in the afternoon may be obtained using the fluid dynamic model 300 based on the measured data for the water-flow velocity at 10 am in the morning and the parameter "slope".

In the following description, a position in the water body at a certain time is referred to as "a time-spatial point", and $P_1 \sim P_5$ as shown in FIG. 2 refer to different time-spatial points differing from each other in position and/or time. The fluid dynamic model 300 may be used to determine simulated data for a water quality indicator of one set of time-spatial points based on measured data for the water quality indicator of another set of time-spatial points and one or more corresponding water body parameters.

It should be appreciated that the fluid dynamic model 300 described herein may be a deterministic model, in which the output (e.g., $S_2$, $S_3$ and $S_4$) is deterministic when the input (e.g., $M_1$ and $M_5$) and the parameter (e.g., the slope) are given. Exemplary fluid dynamic models may comprise of, for example, the Environmental Fluid Dynamics Code (EFDC) or the Water Quality Analysis Simulation Program (WASP).

In the case that the parameter of the fluid dynamic model is able to reflect the actual water environment of the water body (e.g., the actual slope from $P_1$ to $P_5$ equals to the parameter "slope" recorded in the fluid dynamic model), the simulated data output from the fluid dynamic model would conform to the actual measured data.

However, the water environment of the water body may vary with time (e.g., season changes, watershed structure changes), while the water body parameter of the fluid dynamic model does not change adaptively. As a result, the simulation result from the fluid dynamic model may be inaccurate with the actual data in the water body. Therefore, there is a need to optimize the water body parameter of the fluid dynamic model according to the change of the water environment.

The present disclosure incorporates a fluid dynamic model to establish a relation among the measured data of a set of time-spatial points, the water body parameter, and the simulated data of another set of time-spatial points, which may conform well to the actual measured data if the water body parameter is optimized. Therefore, if an inverse process of the fluid dynamic model may be implemented, the optimal water body parameter may be determined using measured data of two sets of time-spatial points.

However, the present disclosure may also assert that the inverse process of the fluid dynamic model may not be directly implemented since the measured data of the two sets of time-spatial points may not be mapped to a unique value of the water body parameter.

The present disclosure is directed to optimization of the water body parameter in which two phases are considered to implement an inverse process of the simulation process of the fluid dynamic model. In the first phase, a value range of the water body parameter may be estimated so that the possible range of the value of the water body parameter is narrowed. In the second phase, an optimal value of the water body parameter may be determined from the estimated value range.

With reference to FIGS. 4-10, some embodiments of the present disclosure will be described below.

Figure 4:
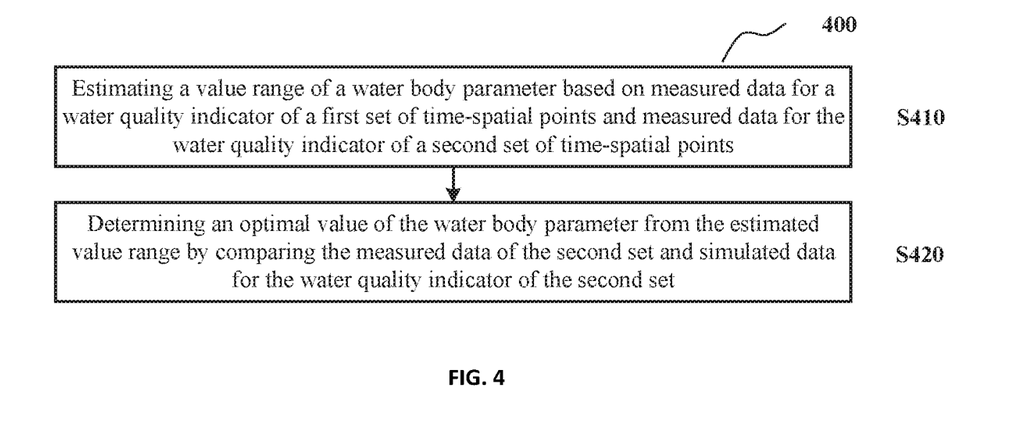
FIG. 4 is a flowchart showing an exemplary computer-implemented method according to an embodiment of the present disclosure.

Now refer to FIG. 4, which is a flowchart showing an exemplary computer-implemented method 400 according to an embodiment of the present disclosure.

As shown in FIG. 4, the method 400 may include a parameter range estimating step S410 and an optimal parameter determining step S420. The parameter range estimating step S410 will be firstly described as follows, and the optimal parameter determining step S420 will be described subsequently.

In step S410, a value range of a water body parameter may be estimated based on measured data for a water quality indicator of a first set of time-spatial points (e.g., $\{M_1, M_5\}$ of set $\{P_1, P_5\}$) and measured data for the water quality indicator of a second set of time-spatial points (e.g., $\{M_2, M_3, M_4\}$ of set $\{P_2, P_3, P_4\}$).

It should be appreciated that the number of time-spatial points in each of the two set is not limited and may be determined according to actual need. Further, there may be only one time-spatial point in one set of time-spatial points. It should also be appreciated that ordinal numbers "first", "second", "third", "fourth" and the like described herein are used in order to avoid confusion among elements, and such terms do not intend to limit the precedence or number of the elements.

In some embodiments, the water quality indicator may be any indicator which indicates the water quality of the water body. As an example, the water quality indicator may be a water-flow velocity, a water temperature or a water level of the water body.

In some embodiments, the water body parameter may be a hydrology parameter indicating the physical property of the water body such as a slope, a roughness coefficient, a wind shear coefficient, a permeable rate or a water quality parameter indicating the chemical property of the water body, such as Chemical Oxygen Demand (COD) or Dissolved Oxygen (DO).

Further, the water body parameter may be related to the water quality indicator. For a given water quality indicator, the water body parameter may be any parameter affecting the water quality indicator. For example, in the case that the water quality indicator is "water-flow velocity", the water body parameter may be at least one of a roughness coefficient, a wind shear coefficient and a permeable rate which may affect the water-flow velocity.

In some embodiments, the value range of the water body parameter may be a range narrowed from a whole range of the possible minimum and maximum water body parameters. The value range estimated in the step S410 may be used in the step S420, so that the optimal value of the water body parameter may be determined from the narrowed range, instead of the whole range of the water body parameter. Therefore, the computation complexity of the step S420 may be reduced due to the step S410.

In some embodiments, the value range of the water body parameter may be estimated using a deep learning model. The details of the deep learning model according embodiments of the present disclosure will be described with reference to FIGS. 5-7.

Figure 5:
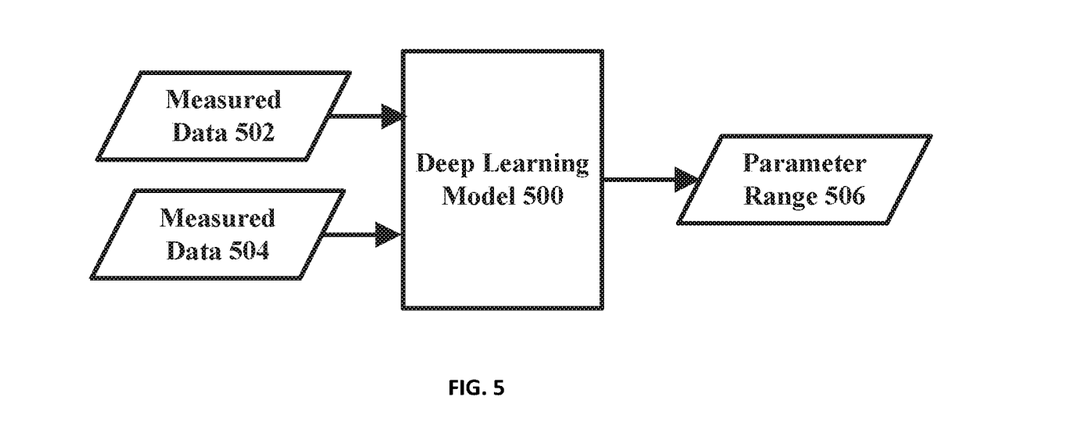
FIG. 5 is a schematic diagram showing an exemplary deep learning model according to an embodiment of the present disclosure.

Now refer to FIG. 5, which is a schematic diagram showing an exemplary deep learning model 500 according to an embodiment of the present disclosure. As shown in FIG. 5, measured data 502 of a first set (e.g., $\{M_1, M_5\}$ of set $\{P_1, P_5\}$) and measured data 504 of a second set (e.g., $\{M_2, M_3, M_4\}$ of set $\{P_2, P_3, P_4\}$) are input to the deep learning model 500 to obtain the parameter range 506 (e.g., the value range of the parameter "slope").

As described in FIG. 3, the measured data 502 (e.g., $\{M_1, M_5\}$ of set $\{P_1, P_5\}$) may be input to the fluid dynamic model 300 to obtain a simulated data of the second set (e.g., $\{S_2, S_3, S_4\}$ of set $\{P_2, P_3, P_4\}$). The simulated data of the second set may be compared with the measured data 504 of the second set (e.g., $\{M_2, M_3, M_4\}$ of set $\{P_2, P_3, P_4\}$) in the optimal parameter determining step S420 of FIG. 4, so as to determine an optimal parameter. The details of the step S420 will be described subsequently.

The deep learning model 500 herein may be regarded as a classification model which classifies the measured data 502 and 504 into a corresponding parameter range 506. It should be appreciated that other classification models (e.g., a classification model in machine learning such as a Support Vector Machine (SVM) and a decision tree) may also be used to estimate the value range from the measured data.

Figure 6:
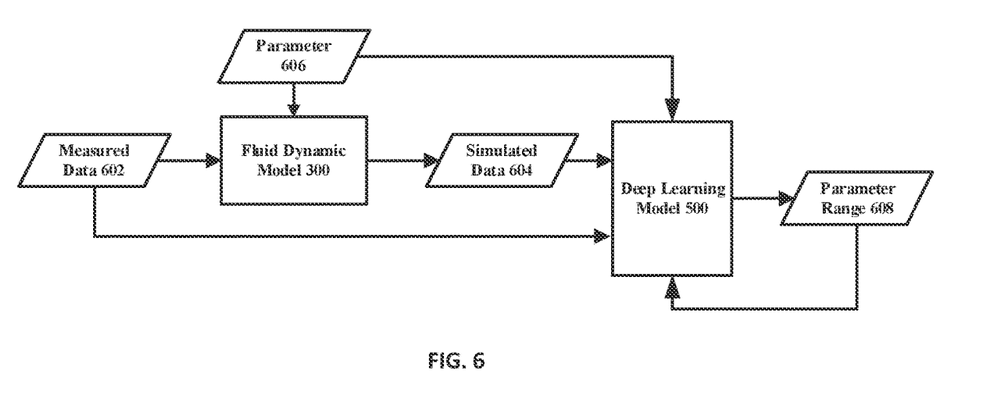
FIG. 6 is a schematic diagram showing an exemplary training process of the deep learning model according to an embodiment of the present disclosure.

In order to use the deep learning model 500 to estimate the parameter range 506, the deep learning model 500 may need to be properly trained in advance. FIG. 6 shows an exemplary training process of the deep learning model 500 according to an embodiment of the present disclosure.

In some embodiments, as shown in FIG. 6, in order to train for the deep learning model 500, the measured data 602 for the water quality indicator (e.g., the water-flow velocity) of a third set of time-spatial points (e.g., $\{M_1', M_5'\}$ of a third set $\{P_1', P_5'\}$) and the parameter 606 of the fluid dynamic model 300 may be used. The parameter 606 may be an initial parameter of the fluid dynamic model 300 (e.g., a parameter recorded in the fluid dynamic model 300) before the training.

Specifically, the measured data 602 is input to the deep learning model 500. The measured data 602 is also input to the fluid dynamic model 300 with the parameter 606 thereof to obtain simulated data 604 for the water quality indicator of a fourth set of time-spatial points (e.g., $\{M_2', M_3', M_4'\}$ of a fourth set $\{P_2', P_3', P_4'\}$). The simulated data 604 is used as another input of the deep learning model 500.

It should be appreciated that the third set and the fourth set may include time-spatial points used for the training phase, which may be either the same as or different from the time-spatial points in the first set or second set in the optimizing phase described with reference to FIG. 4.

Further, the parameter 606 may be used to determine a ground-truth to be compared with the parameter range 608 output from the deep learning model 500, so as to modify the deep learning model 500. For example, a difference between the ground-truth and the parameter range 608 may be used to calculate a back propagation error as an input to the deep learning model 500 to adaptively modify the deep learning model 500.

In embodiments, a data preprocessing may be performed for the training phase. As an example, the whole range of the possible minimum and maximum of the water body parameter may be divided into N intervals, and the data structure of the parameter range 608 may be predetermined as a possibility vector $V=[v_1, v_2, \ldots, v_N]$ with a size of 1×N, wherein $v_i (1 \le i \le N)$ denotes the possibility that the water body parameter is in the $i^{th}$ interval.

The N intervals may be uniformly or non-uniformly divided, depending on the distribution of all possible values of the water body parameter. Further, the number of the divided intervals N may be determined according to the tradeoff of computation complexity and accuracy.

In some embodiment, the parameter 606 of the fluid dynamic model 300 may be normalized for training the deep learning model 500. For example, a water body parameter B may be normalized as $B'=(B-B_{min})/(B_{max}-B_{min})$, so that the whole range $[B_{min}, B_{max}]$ of the water body parameter "slope" may be normalized to [0, 1]. With the normalization, different parameters (e.g., a roughness coefficient or a permeable rate) with different parameter ranges may be similarly used in the training process, so that the computational accuracy may be improved.

Assuming that the whole range of the water body parameter "slope" is normalized to [0, 1] and is uniformly divided into 10 intervals [0, 0.1), [0.1, 0.2), . . . , [0.8, 0.9), [0.9, 1]. In the initial state of the training process, the possibility vector V may be set as a zero vector V=[0, 0, . . . , 0] with a size of 1×10, which means that the possibility that the water body parameter "slope" is in any of the ten intervals equals to zero.

Further, in order to compare the ground-truth of the training process which is determined based on the parameter 606 with the parameter range 608 which is the output of the deep learning model 500, the ground-truth may be set as the same data structure of the parameter range 608. For example, in the case that the parameter 606 (e.g., "slope") equals to 0.25, the possibility vector V' of the parameter 606 may be expressed as V'=[0, 0, 1, 0, . . . , 0] with a size of 1×10, wherein the possibility that the "slope" is in the interval [0.2, 0.3) is "1", and the possibility that the parameter "slope" is in any other interval is "0". The possibility vector V' may be used as the ground-truth to be compared with the parameter range 608.

In some embodiment, in order to obtain more training samples, disturbance variables may be added to the measured data 602 and the parameter 606 respectively. In some embodiment, the disturbance variables may be generated randomly. In some embodiments, the disturbance variable for the measured data 602 may be in a predetermined range so that the measured data 602 with the disturbance variable may also be a possible measured data in the water body. A range of the disturbance variable for the parameter 606 may be similarly determined. In some embodiment, the disturbance variable for the measured data 602 and the disturbance variable for the parameter 606 may be determined separately. In some embodiment, the disturbance variable for the measured data 602 and the disturbance variable for the parameter 606 may have different values.

In some embodiments, after the data preprocessing, the deep learning model 500 may be trained so that the difference between the possibility vectors V and V' (e.g., $\|V-V'\|$) is decreased.

Now returning back to FIG. 5, after the training process described with reference to FIG. 6, the deep learning model 500 may be used to determine the parameter range 506 from measured data 502 and 504.

In some embodiments, the deep learning model 500 may comprise a deep neural network (DNN)-based model. In some embodiments, the deep learning model 500 may be based on at least one of a convolutional neural network (CNN) and a recurrent neural network (RNN). The CNN-based model may be used to establish a spatial relation between a plurality of time-spatial points. The RNN-based model may be used to establish a temporal relation between the plurality of time-spatial points. Further, the DNN-based model may be used to reduce dimensions of data obtained by the deep learning model so as to obtain the parameter range with a desired dimensionality.

The parameter range 506 shown in FIG. 5 denotes the estimated value range of one water body parameter. However, as mentioned above, the water body parameter may be a parameter set to include a plurality of parameters. In this case, the deep learning model 500 may estimate value ranges of the parameter set by training with measured data and the parameter set of the fluid dynamic model 300 with similar training process as described with reference to FIG. 6.

Figure 7A:
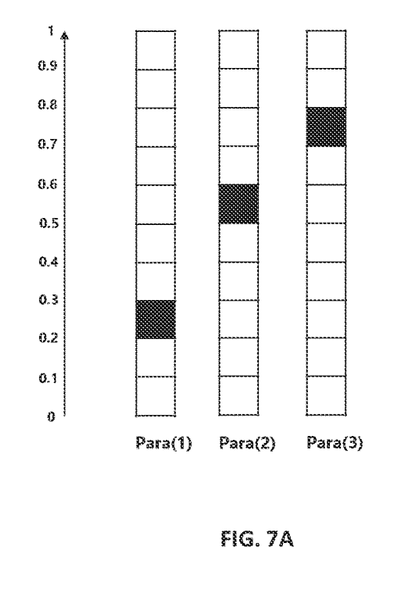
FIGS. 7A and 7B are exemplary graphs of value ranges of a parameter set estimated from the deep learning model according to an embodiment of the present disclosure.
Figure 7B:
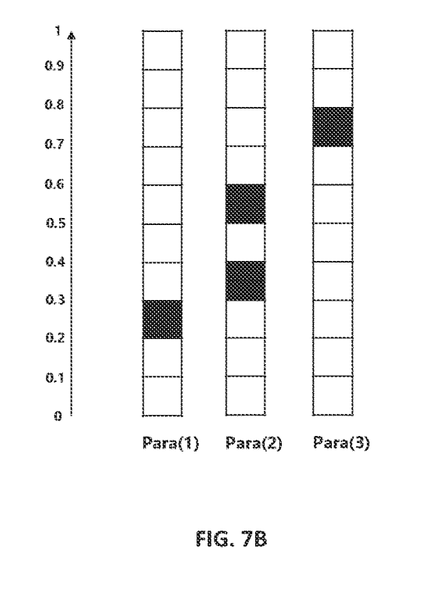

FIGS. 7A and 7B are exemplary graphs of value ranges of a parameter set estimated from the deep learning model 500 according to an embodiment of the present disclosure.

In FIGS. 7A and 7B, the parameter set may include three water body parameters Para(1), Para(2) and Para(3). For example, Para(1), Para(2) and Para(3) may correspond to the slope, the roughness coefficient and the permeable rate respectively and each water body parameter may affect the water quality indicator "water-flow velocity."

FIG. 7A shows a group of estimated value ranges of Para(1), Para(2) and Para(3). For example, a possibility vector $V_1$ of Para(1) is determined from the deep learning model 500 as $V_1$=[0.05,0.05,0.3,0.05,0.05,0.1,0.1,0.1,0.1, 0.1], then the estimated value range of Para(1) may be the interval with the maximum possibility, that is, the interval [0.2, 0.3) with the possibility "0.3" as shown in black in FIG. 7A. The estimated value ranges of Para(2) and Para(3) may be similarly determined as interval [0.5, 0.6) and interval [0.7, 0.8).

In FIG. 7A, each parameter corresponds to a unique value range (black regions shown in FIG. 7A). However, in some embodiments, as shown in FIG. 7B, the value range of the water body parameter may include a plurality of discontinuous ranges.

In FIG. 7B, value ranges of Para(1) and Para(3) are the same as those shown in FIG. 7A. However, as for Para(2), the possibility vector $V_2$ is determined as $V_2$=[0.05,0.05,0.1, 0.2,0.1,0.2,0.05,0.05,0.1,0.1]. That is, there are two intervals [0.3, 0.4) and [0.5, 0.6) with the maximum possibility "0.2". In the present disclosure, even if the estimated value range of the water body parameter includes a plurality of discontinuous ranges, it may be used in the optimal parameter determining step S420 for determining the optimal parameter. The details of the optimal parameter determining step S420 will be described subsequently.

Figure 8:
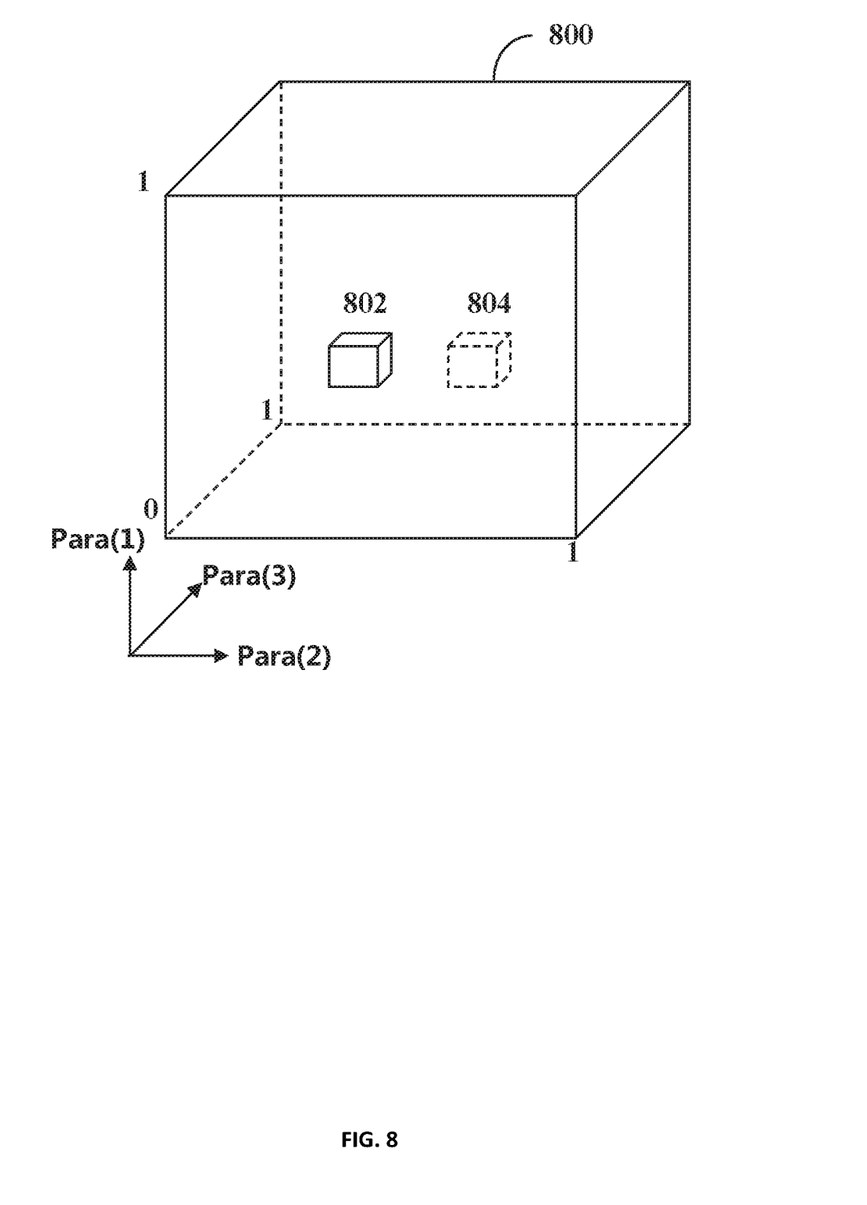
FIG. 8 is an exemplary three-dimension graph showing the estimated value ranges of the parameter set of FIG. 7B.

FIG. 8 is an exemplary three-dimensional graph showing the estimated value ranges of the parameter set {Para(1), Para(2), Para(3)} of FIG. 7B, wherein each dimension of the cube 800 corresponds to a value range of one water body parameter in the parameter set. Cube 802 may correspond to interval [0.2, 0.3) for Para(1), interval [0.3, 0.4) for Para(2) and interval [0.7, 0.8) for Para(3). Further, cube 804 may correspond to interval [0.2, 0.3) for Para(1), interval [0.5, 0.6) for Para(2) and interval [0.7, 0.8) for Para(3).

The estimated value ranges of the parameter set may be illustrated by the two cubes 802 and 804. As shown in FIG. 8, the estimated value ranges of the parameter set may be narrowed (e.g., from the cube 800 to the cubes 802 and 804) in the parameter estimating phase, thus the computation complexity in the subsequent optimal parameter determining phase may be decreased.

Now returning back to FIG. 4, in the optimal parameter determining step S420, an optimal value of the water body parameter may be determined from the value range estimated in step S410 by comparing the measured data of the second set with simulated data for the water quality indicator of the second set. Further, as mentioned above, the simulated data of the second set is obtained based on a fluid dynamic model using the measured data of the first set as an input of the fluid dynamic model and using a value in the estimated value range as a parameter of the fluid dynamic model.

In some embodiments, the optimal value of the water body parameter may be the optimum in the estimated value range so that the simulated data of the second set is the closest to the measured data of the second set. In some embodiments, the optimal value may be one or more values in the estimated value range which satisfy a predetermined condition, for example, over a predetermined threshold after a predetermined time of iterations.

In some embodiments, the optimal value of the water body parameter may be determined from the estimated value range using an optimization model, such as a linear regression model in machine learning.

Figure 9:
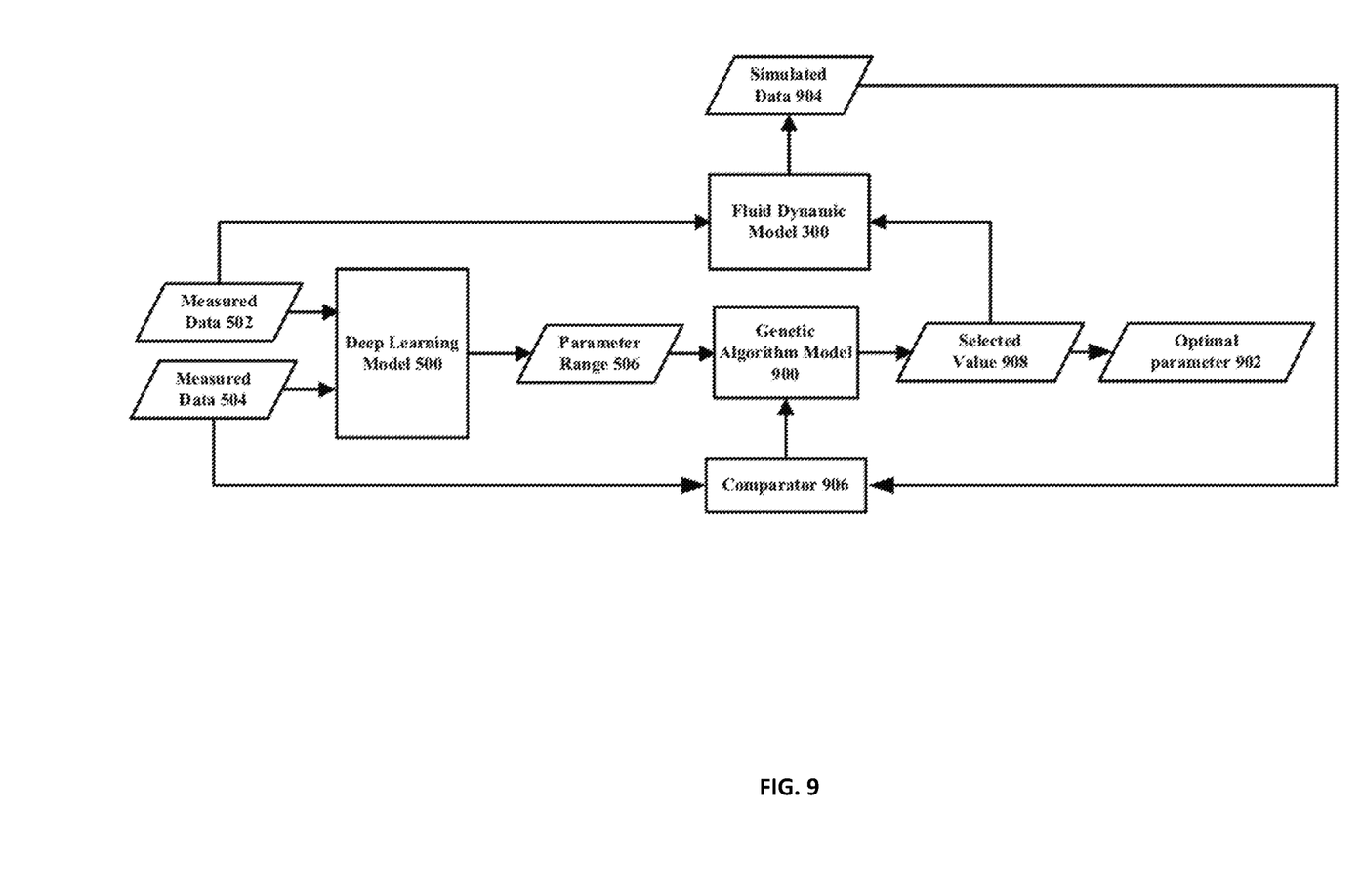
FIG. 9 is a schematic diagram showing an exemplary genetic algorithm model according to an embodiment of the present disclosure.

In some embodiments, as shown in FIG. 9, the optimal value of the water body parameter may be determined from the estimated value range using a genetic algorithm model 900.

In FIG. 9, the measured data 502, 504, the deep learning model 500 and the parameter range 506 are the same as those described with reference to FIG. 5 as an exemplary implementation of the parameter range estimating step S410. Further, as mentioned above, other classification models may replace the deep learning model 500 in FIG. 9 to implement the parameter range estimating step S410.

As shown in FIG. 9, the parameter range 506 is input to the genetic algorithm model 900 to determine the optimal parameter 902, by comparing the measured data 504 with the simulated data 904 using a comparator 906. In some embodiments, the measured data 504 and the simulated data 904 may be compared based on a difference between the measured data 504 and the simulated data 904. Further, the simulated data 904 is obtained based on the fluid dynamic model 300 using the measured data 502 as an input and using a selected value 908 in the parameter range 506 as the parameter of the fluid dynamic model 300.

In some embodiments, a fitness may be used to determine the optimal parameter 902, which may be calculated based on a difference between the measured data 504 and the simulated data 904. For example, if the selected value 908 in the parameter range 506 has the best fitness compared with the fitness of all other values in the parameter range 506, the selected value 908 may be determined as the optimal parameter 902.

An exemplary directional genetic algorithm will be described below as an implementation of the genetic algorithm model 900 of the present disclosure. It should be appreciated that other genetic algorithms may also be used to implement the genetic algorithm model 900.

As discussed in FIG. 8, the parameter range 506 may correspond to the cubes 802 and 804. The directional genetic algorithm may search for an optimal parameter value in each cube and compare the optimal parameter values searched in each cube to obtain the optimal parameter 902.

Specifically, for cube 802, a sample $A_1$ in the cube 802 is selected. Then, a point $A_2$ which is the nearest to $A_1$ with a higher fitness than $A_1$ is chosen from the cube 802. Further, a point $A_1'$ is obtained by $A_1'=A_2+c(A_2-A_1)$, wherein c is a randomly chosen constant from a predetermined interval, e.g., 0.5<c<1.5. Further, $A_1'$ is randomly deviated a little in the cube 802 to express a mutation. The fitness of $A_1$ is calculated based on a difference between the measured data 504 and the simulated data 904 corresponding to $A_1$. The fitness of $A_1'$ is similarly calculated. The fitness of $A_1$ and $A_1'$ is judged to retain the one with a better fitness. Further, some samples in the cube 802 are discarded under certain conditions according to the fitness of each sample in the cube 802.

By repeating the above process, a sample in the cube 802 with the best fitness will remain as an optimal parameter.

Similar process may be performed to cube 804, and an optimal parameter will be obtained from the cube 804. The optimal parameter 902 may be determined as the one with a better fitness of the two optimal parameters determined from the cubes 802 and 804.

After determining the optimal parameter 902, the parameter of the fluid dynamic model 300 may be updated with the optimal parameter 902 to perform simulation more accurately.

In some embodiments, the parameter of the fluid dynamic model may be updated regularly. For example, the method 400 described in FIG. 4 may be performed regularly, so that the parameter of the fluid dynamic model would catch up with the change of the water environment.

Figure 10:
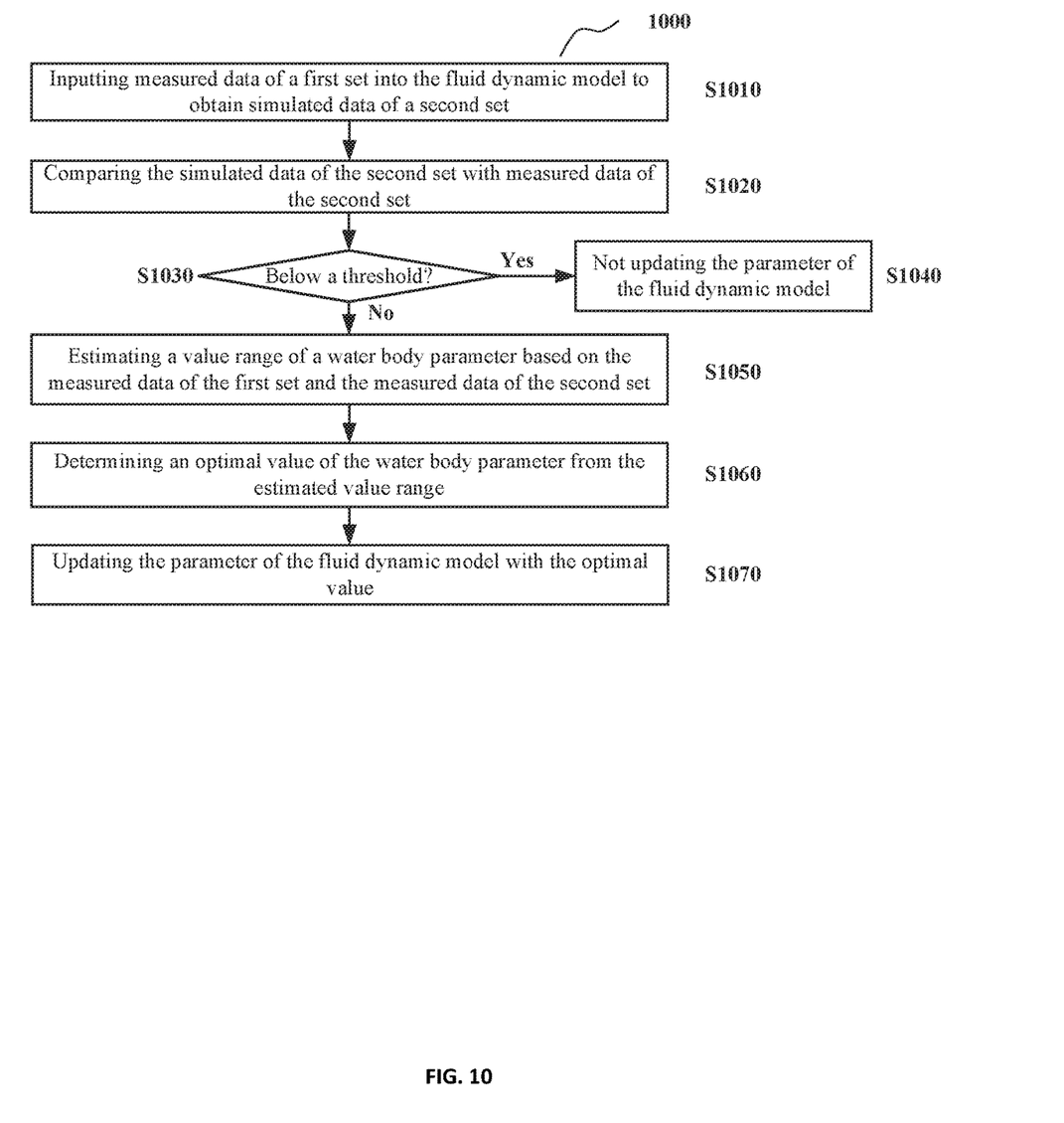
FIG. 10 is a flowchart showing an exemplary parameter updating method for the parameter of the fluid dynamic model according to an embodiment of the present disclosure.

In some embodiments, the parameter of the fluid dynamic model may be updated adaptively according to the measured data. FIG. 10 shows an exemplary parameter updating method 1000 for the parameter of the fluid dynamic model according to an embodiment of the present disclosure.

In step S1010, measured data of a first set (e.g., $\{M_1, M_5\}$ of set $\{P_1, P_5\}$) is inputted into the fluid dynamic model. The fluid dynamic model determines simulated data of a second set (e.g., $\{S_2, S_3, S_4\}$ of set $\{P_2, P_3, P_4\}$) using the input measured data of the first set and the water body parameter of the fluid dynamic model.

In step S1020, the simulated data of the second set (e.g., $\{S_2, S_3, S_4\}$ of set $\{P_2, P_3, P_4\}$) is compared with the measured data of the second set (e.g., $\{M_2, M_3, M_4\}$ of set $\{P_2, P_3, P_4\}$).

In step S1030, if a difference between the simulated data (e.g., $\{S_2, S_3, S_4\}$) and the measured data (e.g., $\{M_2, M_3, M_4\}$) is below a predetermined threshold ("Yes" in S1030), it is determined that the parameter of the fluid dynamic model used to obtain the simulated data in step S1010 is able to reflect the actual water environment of the water body, thus may not be necessary to be updated. In this case, the method proceeds to step S1040, in which it is decided not to update the parameter of the fluid dynamic model.

On the other hand, in step S1030, if a difference between the simulated data (e.g., $\{S_2, S_3, S_4\}$) and the measured data (e.g., $\{M_2, M_3, M_4\}$) is not below a predetermined threshold ("No" in S1030), it is determined that the parameter of the fluid dynamic model used to obtain the simulated data in step S1010 is not able to reflect the actual water environment of the water body, and may need to be updated. In this case, the method proceeds to the parameter range estimating step S1050 and the optimal parameter determining step S1060. The steps S1050 and S1060 may correspond to the steps S410 and S420 in FIG. 4 respectively and the detailed descriptions for steps S1050 and S1060 are omitted here.

In step S1070, the parameter of the fluid dynamic model is updated by the optimal value determined in step S1060.

According to the parameter updating method 1000, the parameter of the fluid dynamic model may be updated adaptively according to the measured data in the water body. Therefore, the parameter may catch up with the change of the water environment adaptively so that the fluid dynamic model may perform simulation more accurately.

The present disclosure may be a system, a method or a computer program product at various possible technical detail levels of integration. The computer program product may include a computer readable storage medium (or media) having computer readable program instructions thereon for causing a processor to carry out aspects of the present disclosure.

According to an embodiment of the present disclosure, there is provided a system, which may comprise one or more processors and a memory coupled to at least one of the one or more processors. The system may further comprise a set of computer program instructions stored in the memory and executed by at least one of the one or more processors in order to perform actions of estimating a value range of a water body parameter based on measured data for a water quality indicator of a first set of time-spatial points and measured data for the water quality indicator of a second set of time-spatial points; and determining an optimal value of the water body parameter from the estimated value range by comparing the measured data for the water quality indicator of the second set and simulated data for the water quality indicator of the second set, wherein the simulated data for the water quality indicator of the second set is obtained based on a fluid dynamic model using the measured data for the water quality indicator of the first set as an input of the fluid dynamic model and using a value in the estimated value range as a parameter of the fluid dynamic model.

According to an embodiment of the present disclosure, there is provided a computer program product. The computer program product may comprise a computer readable storage medium having program instructions embodied therewith. The program instructions may be executable by a device to perform a method. The method may comprise estimating a value range of a water body parameter based on measured data for a water quality indicator of a first set of time-spatial points and measured data for the water quality indicator of a second set of time-spatial points; and determining an optimal value of the water body parameter from the estimated value range by comparing the measured data for the water quality indicator of the second set and simulated data for the water quality indicator of the second set, wherein the simulated data for the water quality indicator of the second set is obtained based on a fluid dynamic model using the measured data for the water quality indicator of the first set as an input of the fluid dynamic model and using a value in the estimated value range as a parameter of the fluid dynamic model.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
   estimating a value range of a water body parameter based on measured data for a water quality indicator of a first set of time-spatial points and measured data for a water quality indicator of a second set of time-spatial points, wherein the value range of the water body parameter is estimated using a decision tree,
   wherein a deep learning model is trained by measured data for a water quality indicator of a third set of time-spatial points and an initial parameter of a fluid dynamic model, wherein disturbance variables are added to the measured data for the water quality indicator of the third set of time-spatial points and the initial parameter of the fluid dynamic model respectively to obtain training samples for the deep learning model, wherein the disturbance variables for the measured data for the water quality indicator of the third set of time-spatial points are in a predetermined range so that the measured data for the water quality indicator of the third set of time-spatial points with the disturbance variable is a possible measured data in the water body; and
   determining an optimal value of the water body parameter from the estimated value range by comparing the measured data for the water quality indicator of the second set and simulated data for the water quality indicator of the second set,
   wherein the simulated data for the water quality indicator of the second set is obtained based on the fluid dynamic model using the measured data for the water quality indicator of the first set as an input of the fluid dynamic model and using a value in the estimated value range as a parameter of the fluid dynamic model.

2. The computer-implemented method according to claim 1, wherein estimating the value range of the water body parameter further comprises a support vector machine.

3. The computer-implemented method according to claim 2, wherein the deep learning model is based on at least one of a convolutional neural network and a recurrent neural network.

4. The computer-implemented method according to claim 2, wherein the measured data for the water quality indicator of the third set of time-spatial points and simulated data for a water quality indicator of a fourth set of time-spatial points are used as inputs of the deep learning model, and the initial parameter of the fluid dynamic model is used to determine a ground-truth to be compared with a value range output from the deep learning model, and wherein the simulated data for the water quality indicator of the fourth set is obtained based on the fluid dynamic model using the measured data for the water quality indicator of the third set and the initial parameter of the fluid dynamic model.

5. The computer-implemented method according to claim 4, wherein the deep learning model is trained so that a difference between the ground-truth and the value range output from the deep learning model is decreased.

6. The computer-implemented method according to claim 4, wherein the initial parameter of the fluid dynamic model is normalized for training the deep learning model.

7. The computer-implemented method according to claim 1, wherein the optimal value of the water body parameter is determined from the estimated value range using a genetic algorithm.

8. The computer-implemented method according to claim 1, wherein the value range of the water body parameter includes a plurality of discontinuous ranges.

9. The computer-implemented method according to claim 1, further comprising:
updating the parameter of the fluid dynamic model with the optimal value in response to a difference between the measured data for the water quality indicator of the second set and the simulated data for the water quality indicator of the second set being above a predetermined threshold.

10. A system comprising:
one or more processors;
a memory coupled to at least one of the one or more processors;
a set of computer program instructions stored in the memory and executed by at least one of the one or more processors in order to perform actions of:
estimating a value range of a water body parameter based on measured data for a water quality indicator of a first set of time-spatial points and measured data for a water quality indicator of a second set of time-spatial points, wherein the value range of the water body parameter is estimated using a decision tree,
wherein a deep learning model is trained by measured data for a water quality indicator of a third set of time-spatial points and an initial parameter of a fluid dynamic model, wherein disturbance variables are added to the measured data for the water quality indicator of the third set of time-spatial points and the initial parameter of the fluid dynamic model respectively to obtain training samples for the deep learning model, wherein the disturbance variables for the measured data for the water quality indicator of the third set of time-spatial points are in a predetermined range so that the measured data for the water quality indicator of the third set of time-spatial points with the disturbance variable is a possible measured data in the water body; and
determining an optimal value of the water body parameter from the estimated value range by comparing the measured data for the water quality indicator of the second set and simulated data for the water quality indicator of the second set,
wherein the simulated data for the water quality indicator of the second set is obtained based on the fluid dynamic model using the measured data for the water quality indicator of the first set as an input of the fluid dynamic model and using a value in the estimated value range as a parameter of the fluid dynamic model.

11. The system according to claim 10, wherein estimating the value range of the water body parameter further comprises a support vector machine.

12. The system according to claim 11, wherein the measured data for the water quality indicator of the third set of time-spatial points and simulated data for a water quality indicator of a fourth set of time-spatial points are used as inputs of the deep learning model, and the initial parameter of the fluid dynamic model is used to determine a ground-truth to be compared with a value range output from the deep learning model, and wherein the simulated data for the water quality indicator of the fourth set is obtained based on the fluid dynamic model using the measured data for the water quality indicator of the third set and the initial parameter of the fluid dynamic model.

13. The system according to claim 12, wherein the deep learning model is trained so that a difference between the ground-truth and the value range output from the deep learning model is decreased.

14. The system according to claim 10, wherein the optimal value of the water body parameter is determined from the estimated value range using a genetic algorithm.

15. A computer program product comprising a computer readable storage medium having program instructions embodied therewith, wherein the program instructions being executable by a device to perform a method comprising:
estimating a value range of a water body parameter based on measured data for a water quality indicator of a first set of time-spatial points and measured data for a water quality indicator of a second set of time-spatial points, wherein the value range of the water body parameter is estimated using a decision tree,
wherein a deep learning model is trained by measured data for a water quality indicator of a third set of time-spatial points and an initial parameter of a fluid dynamic model, wherein disturbance variables are added to the measured data for the water quality indicator of the third set of time-spatial points and the initial parameter of the fluid dynamic model respectively to obtain training samples for the deep learning model, wherein the disturbance variables for the measured data for the water quality indicator of the third set of time-spatial points are in a predetermined range so that the measured data for the water quality indicator of the third set of time-spatial points with the disturbance variable is a possible measured data in the water body; and
determining an optimal value of the water body parameter from the estimated value range by comparing the measured data for the water quality indicator of the second set and simulated data for the water quality indicator of the second set, wherein the simulated data for the water quality indicator of the second set is obtained based on the fluid dynamic model using the measured data for the water quality indicator of the first set as an input of the fluid dynamic model and using a value in the estimated value range as a parameter of the fluid dynamic model.

16. The computer program product according to claim 15, wherein estimating the value range of the water body parameter further comprises a support vector machine.

17. The computer program product according to claim 16, wherein the measured data for the water quality indicator of the third set of time-spatial points and simulated data for a water quality indicator of a fourth set of time-spatial points are used as inputs of the deep learning model, and the initial parameter of the fluid dynamic model is used to determine a ground-truth to be compared with a value range output from the deep learning model, and wherein the simulated data for the water quality indicator of the fourth set is obtained based on the fluid dynamic model using the measured data for the water quality indicator of the third set and the initial parameter of the fluid dynamic model.

18. The computer program product according to claim 17, wherein the deep learning model is trained so that a difference between the ground-truth and the value range output from the deep learning model is decreased.

19. The computer program product according to claim 15, wherein the optimal value of the water body parameter is determined from the estimated value range using a genetic algorithm.

\* \* \* \* \*